United States Patent [19]

Kwon

[11] Patent Number: 4,461,996
[45] Date of Patent: Jul. 24, 1984

[54] NUCLEAR MAGNETIC RESONANCE CELL HAVING IMPROVED TEMPERATURE SENSITIVITY AND METHOD FOR MANUFACTURING SAME

[75] Inventor: Tae M. Kwon, Thousand Oaks, Calif.

[73] Assignee: Litton Systems, Inc., Beverly Hills, Calif.

[21] Appl. No.: 405,807

[22] Filed: Aug. 6, 1982

[51] Int. Cl.³ ............................................. G01R 33/08
[52] U.S. Cl. ..................................... 324/315; 324/300
[58] Field of Search ................ 324/300, 315, 302, 301

[56] References Cited

U.S. PATENT DOCUMENTS 3,621,378 11/1971 Kleiman ............................... 324/315
4,157,495 6/1979 Grove ................................... 324/302

Primary Examiner—Michael J. Tokar
Attorney, Agent, or Firm—Gerald L. Cline

[57] ABSTRACT

A nuclear magnetic resonance (NMR) cell for use in a gyro is shown which is maintained at a predetermined temperature, established by testing. Testing of each cell is conducted by heating the cell within a gyro to a series of temperatures and plotting the gyro bias (degrees/time) for each temperature within the series. At one temperature the magnitude of gyro bias will no longer increase but will start to decrease. This temperature turning point is the temperature at which the NMR cell should be maintained for zero temperature sensitivity of the gyro.

17 Claims, 6 Drawing Figures

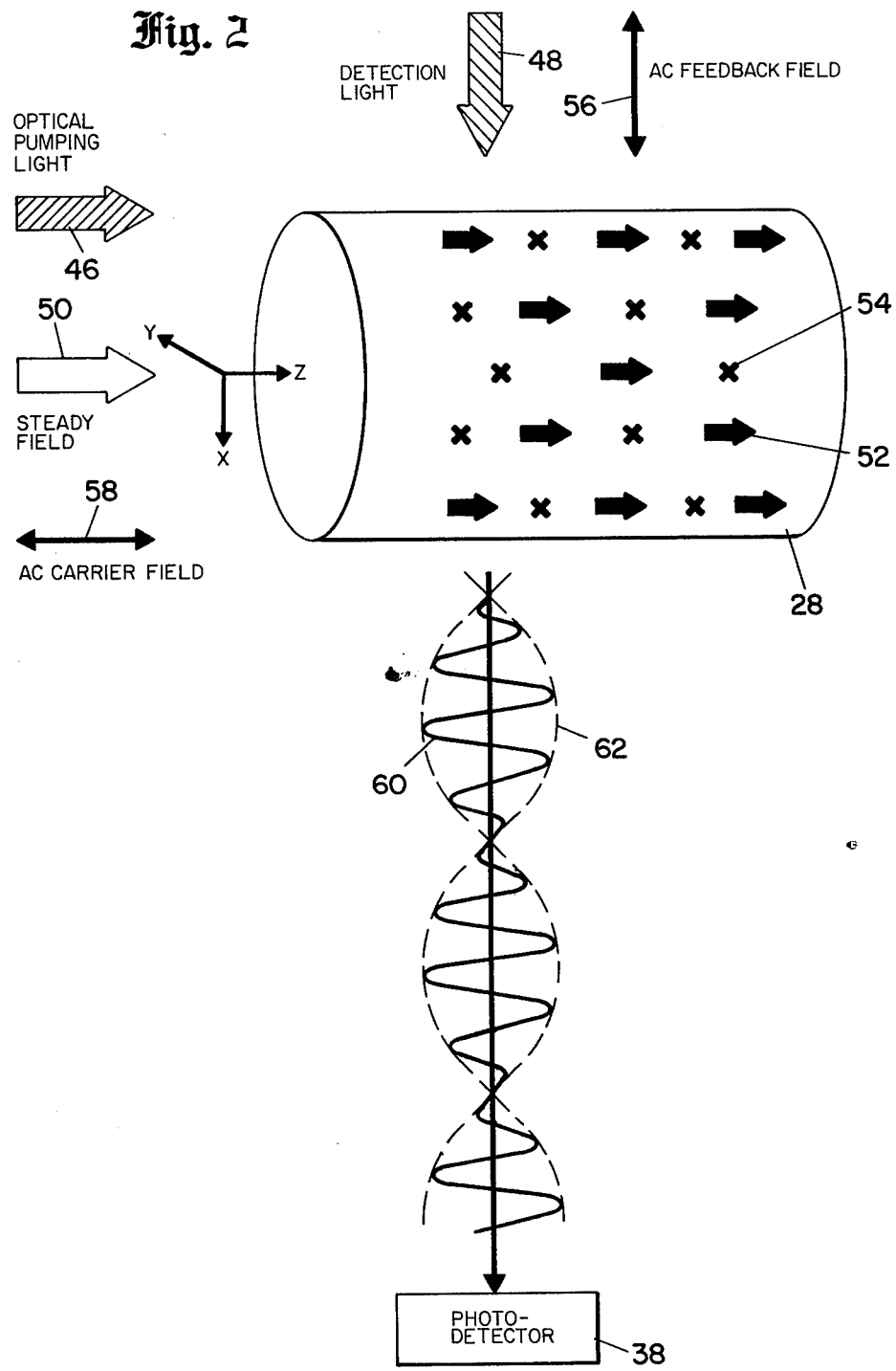

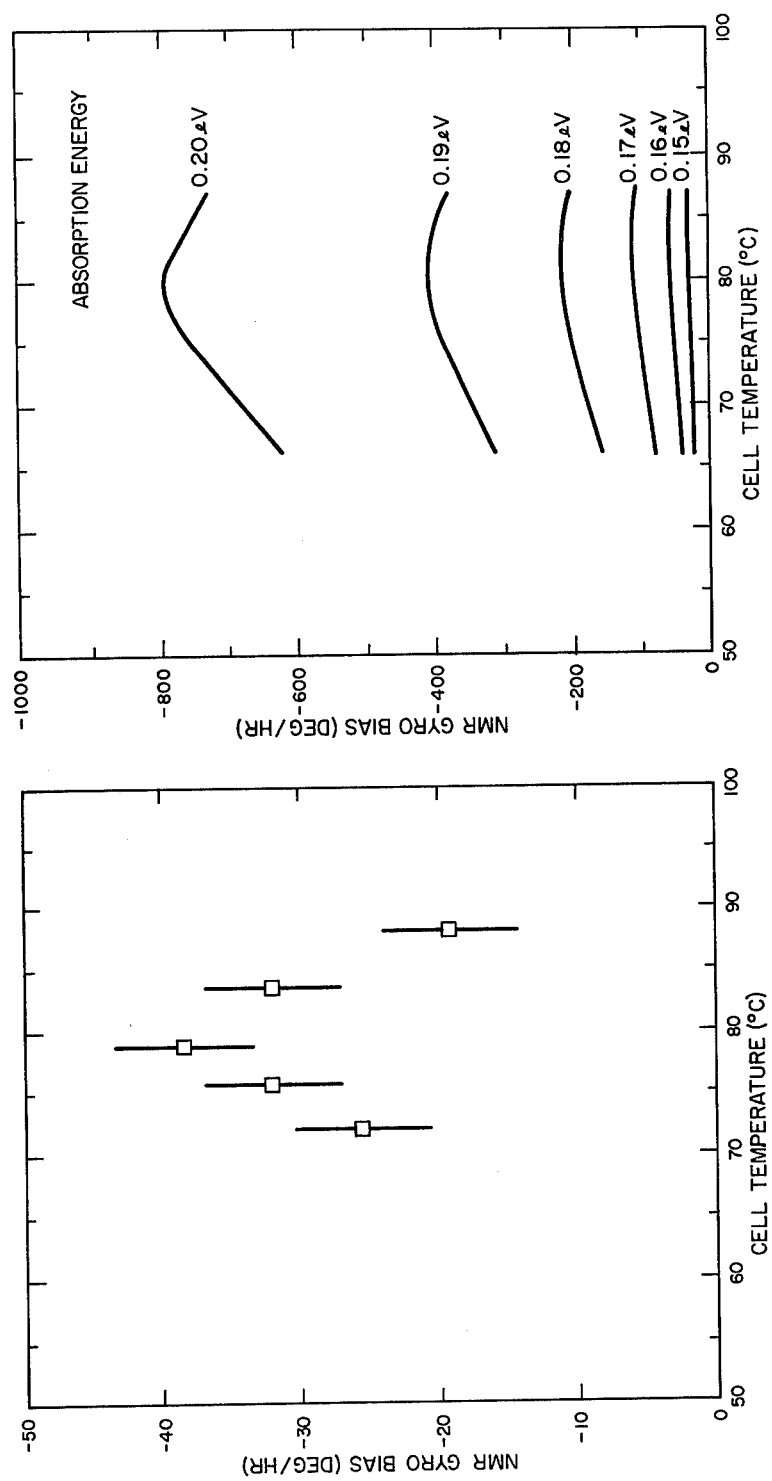

4,461,996

NUCLEAR MAGNETIC RESONANCE CELL HAVING IMPROVED TEMPERATURE SENSITIVITY AND METHOD FOR MANUFACTURING SAME

The Government has rights in this invention pursuant to Contract No. F49620-77-C-0047 awarded by the Air Force Office of Scientific Research.

TECHNICAL FIELD

This invention relates to the creation and detection of nuclear magnetic resonance and, more particularly, to magnetic resonance devices having improved temperature sensitivity and to a method for manufacturing such devices.

BACKGROUND OF THE INVENTION

The utilization of nuclear magnetic resonance (hereinafter referred to as "NMR") to create a gyroscope is disclosed in U.S. Letters Pat. No. 4,157,495 which issued June 5, 1979 and which is assigned to the same assignee as the present invention.

The gyroscope disclosed therein operates on the principle of sensing inertial angular rotation rate or angular displacement about a sensitive axis of the device as a shift in the Larmor precession frequency or phase, respectively, of one or more isotopes that possess nuclear magnetic moments.

The gyroscope is composed of an angular rotation sensor and associated electronics. The principal elements of the sensor are a light source, an NMR cell, a photodetector, a set of magnetic shields and a set of magnetic field coils. The principal elements of the electronics are signal processing circuits for extracting the Larmor precession frequency and phase information as well as circuits for generating and controlling various magnetic fields, both steady and varying sinusoidally with time, that are necessary for the proper operation of the device.

The NMR cell is mounted within a set of magnetic shields in order to attenuate external magnetic fields to acceptable low levels. Magnetic field coils are used to apply uniform magnetic fields to the NMR cell. Both a steady field and an AC carrier field are applied along the sensitive axis of the device and an AC feedback field is applied along one of the transverse axes. The DC magnetic fields along both transverse axes are controlled to be substantially zero. The NMR cell contains a single alkali metal vapor, such a rubidium, together with two isotopes of one or more noble gases, such as krypton or xenon. One or more buffer gases such as helium or nitrogen may also be contained in the cell.

The NMR cell is illuminated by a beam of circularly polarized light that originates from a source such as a rubidium lamp and which passes through the cell at an angle with respect to the steady magnetic field. Absorption of some of this light causes the atomic magnetic moments of the rubidium atoms to be partly aligned in the direction of the steady magnetic field. This alignment is partly transferred to the nuclear magnetic moments of the noble gases, and these moments are caused to precess about the direction of the steady magnetic filed, which in turn creates magnetic fields that rotate at the respective Larmor precession frequencies of the two noble gases. These rotating fields modulate the precessional motions of the rubidium magnetic moments, which in turn produce corresponding modulations of the transmitted light, thereby making it possible to optically detect the Larmor precession frequencies of the two noble gases.

The modulations of the light intensity are converted into electrical signals by a photodetector, and these signals are then electronically demodulated and filtered to provide signals at the Larmor precession frequencies of the two noble gases. The difference between the two precession frequencies is used to accurately control the steady magnetic field so that it is constant. One of the noble gas precession frequencies is subtracted from a precision reference frequency. The resulting difference frequency is a measure of the angular rotation rate of the gyroscope. The magnitude of an individual nuclear magnetic moment is extremely small and the natural equilibrium condition is one in which a nearly random orientation of moments exists in an ensemble of atoms. Techniques must be used to orient a significant fraction of these magnetic moments in a single direction so that a macroscopic magnetic moment, and consequently a measurable signal, will be produced.

The aligned magnetic moments of the single alkali metal system and of both noble gas systems of atoms are subject to relaxation mechanisms which cause their alignments to decay with time towards their natural equilibrium condition of random orientation. Each system of moments is characterized by a relaxation time constant which depends on the kinds and quantities of all other constituents and upon the total environment in the NMR cell. The steady state fractional alignment of each system of moments is a function of both the pumping rate and the relaxation time for the system, with larger fractional alignments, hence larger signal amplitudes, being achieved when the relaxation times are also long.

A number of prior art techniques exist to achieve longer relaxation times. In one of the techniques, a suitable amount of a buffer gas such as helium or nitrogen is also contained in the cell in order to reduce the relaxation effects due to interactions of the magnetic moments with the walls of the cell. In another technique, particular isotopes of particular noble gases are chosen as the nuclear magnetic moment gases specifically for their long relaxation times. However, a problem still exists since certain, otherwise desirable magnetic moment gases have relaxation times too short to provide a practical device.

Two co-pending patent applications which address this problem and which are assigned to the same assignee as the present invention include Ser. No. 307,995 filed Oct. 2, 1981, for an Improved Magnetic Resonance Cell And Method For Its Fabrication by T. M. Kwon and W. P. Debley, and Ser. No. 307,996 filed Oct. 2, 1981 for An Improved Magnetic Resonance Cell by T. M. Kwon and C. H. Volk.

In addition to the desire to lengthen the relaxation times of the NMR cell, it is also desirable to improve the temperature sensitivity of the cell. It is known that an NMR cell will undergo a drift measured in degrees per hour. That is, by placing an NMR cell within a gyroscope upon a fixed platform and plotting the apparent angular rotational rate of the gyroscope in degrees, one will find that the output of the gyroscope produces an indication of rotation even though the gyroscope has been fixed. This apparent rotation is referred to as the gyro bias. It has been found that the gyro bias is influenced by temperature.

SUMMARY OF THE INVENTION

Accordingly, an object of the present invention is to reduce the temperature sensitivity of an NMR gyro.

Another object of the invention is to eliminate the susceptibility of gyro bias to temperature change.

In accomplishing these and other objects, there is provided an NMR cell in which two isotopes of the same noble gas have been introduced. A method is disclosed for measuring, over a predetermined temperature range, the NMR gyro bias for the particular cell. It has been found, unexpectedly, that a plot of this gyro bias versus temperature does not produce an expected line having no maximum or minimum value. Rather, the magnitude of the bias increases to a maximum value at a particular temperature, reverses itself, and then decreases.

Thus, the method taught by the present invention, to reduce temperature sensitivity of an NMR cell, is accomplished by measuring a particular cell bias over a specific temperature range. Once this is done, the temperature at which the cell's bias stops increasing and begins to decrease is be established. Having established this temperature, the cell is then placed in an oven whose temperature is maintained at this established value to within a narrow range. This reduces the temperature sensitivity of the gyro bias to nearly zero, if not zero.

The temperature range may be broadened by proper cell selection. It has also been found that a cell with a low adsorption energy value will have a flatter bias versus temperature curve which permits the maintenance of a broader temperature range to maintain the same temperature sensitivity. Cells with a low adsorption energy may be obtained by coating the inner cell wall with a layer of alkali metal hydride.

Using the discoveries of the present invention, one may simply maintain an NMR cell at an established temperature to reduce its temperature sensitivity, or, in some embodiments, it may be desirable to build into the gyro electronics an electrical feedback circuit which senses the temperature of the NMR cell and makes a predetermined adjustment to the output signal of the NMR cell to correct for the drift of the angular rotational rate of the gyro. The advantage of using such a feedback is that the temperature of the cell may be retained within a still broader tolerance range than the range required when the cell is maintained at a temperature where its gyro bias is near zero degrees per hour.

DESCRIPTION OF THE DRAWINGS

A better understanding of the invention will be had after consideration of the specification and accompanying drawings wherein:

FIG. 2 is a conceptual diagram illustrating the operation of an NMR cell;

FIG. 3 is a plot of experimental results showing NMR gyro bias (deg/hr) versus cell temperature (°C.);

FIG. 4 is a family of calculated curves showing NMR gyro basis (deg/hr) versus cell temperature (°C.) for various adsorption energy values;

DETAILED DESCRIPTION OF THE PREFERRED EMBODIMENTS

Figure 1:
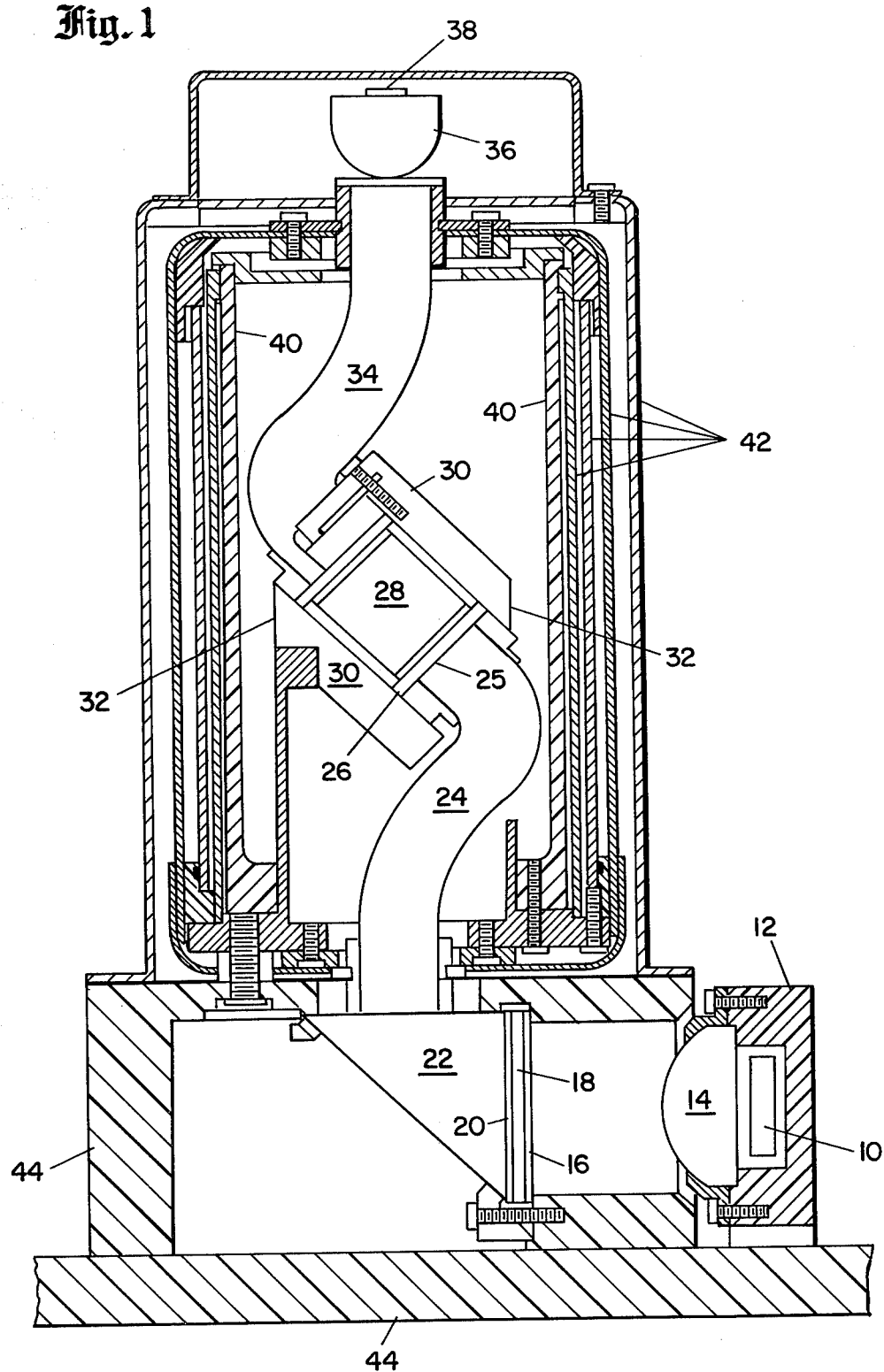
FIG. 1 is a sectional view showing the component of a typical NMR gyro sensor incorporating the NMR cell of the present invention.

Referring now to the drawings, FIG. 1 shows the physical arrangement of components of an NMR gyro assembly including a rubidium vapor lamp 10, which is excited by a high frequency power source, used to emit light containing the spectral lines of rubidium. This lamp is similar in design to that descried by Bell, Bloom and Lynch (Rev. Sci. Instr. 32,688 [1961]). The lamp 10 is housed in an enclosure 12 which is used to maintain the lamp at an elevated temperature suitable for maximum light emission. The light passes through a glass condenser lens 14 and through a plastic fresnel collimating lens 16 before passing through an optical interference filter 18. This filter is designed to transmit most of the 794.7 nanometer wavelength light from one spectral line of the rubidium while blocking most of the 780.0 nanometer wavelength light from an adjacent spectral line. The filtered light passes through a second fresnel collimating lens 20, is reflected in a prism 22 to change its direction and converges on the end of an input fiber optics bundle 24. This fiber optics bundle then transmits the light towards the center of the device and makes a bend so that the light leaves the end 25 of the bundle 24 at an angle of approximately 45 degrees relative to the vertical of the drawing. The vertical axis, as shown in the drawing, is designated as the z-axis. The x-axis is defined as pointing left to right in the drawing. Thus, FIG. 1 is a sectional drawing in the x–z plane. The light leaving the bundle 24 passes through a circular polarizer 26, and enters an NMR cell 28.

The NMR cell 28 is a sealed, optically transparent, glass spherical enclosure, shown cylindrical for clarity of illustration, containing a small quantity of isotopically enriched rubidium-87 metal, approximately 0.5 torr of isotopically enriched xenon-129 gas, approximately 2.0 torr of isotopically enriched xenon-131 gas, and a buffer gas consisting of about 40 torr of nitrogen and 100 torr of helium-4. These are introduced into the cell in the order stated while the cell is attached to a vacuum filling station and then sealed off.

The cell 28 is mounted in a temperature controlled alumina oven 30 which is heated and controlled by a resistance band heater 32 that uses a high frequency power source, not shown. The oven is maintained at a specific temperature pecular to the cell 28 to be described hereinbelow. Approximately one-half of the light that is not absorbed in the cell 28 enters an output fiber optics bundle 34 and passes through a lens 36 to a silicon photodetector 38. Other components shown in this drawing are a magnetic field coil structure 40, a set of several layers of magnetic shielding 42, designed to attenicate the influence of external magnetic fields, and a supporting structure 44.

FIG. 2 is a conceptual diagram illustrating for each of the noble gases, the processes of optical pumping, and the modulation of the intensity of the light that is transmitted through the NMR cell. Because these processes are so similar for the two noble gases, they are illustrated and described for only one of the two noble gases. The circularly polarized light which enters the NMR cell 28 has a component 46 along the z-axis, which is referred to as optical pumping light, and a component 48 along the x-axis, which is referred to as detection light. The light beams 46 and 48 may be formed from the same source and then split by the fiber optics bundle, for example, or they may be generated by two separate sources. Through the interactions of the optical pumping light 46 and a steady magnetic field 50, generated by the coils, not shown, on coil structure 40, the rubidium atoms 52 have their magnetic moments aligned preferentially in the z-direction. By a spin exchange process this magnetic moment alignment is transferred from the rubidium atoms 52 to the noble gas nuclei 54.

A sinusoidal AC feedback magnetic field 56 that is matched in frequency and phase to the Larmor precession frequency of the collective magnetic moment of the noble gas nuclei 54 is applied in the x-direction and serves to torque the magnetic moment of these nuclei to the x-y plane. This component of noble gas nuclear magnetic moment then precesses in the x-y plane at the noble gas Larmor precession frequency $\omega$ about the steady magnetic field 50. This precessing nuclear magnetic moment component creates a nuclear precession magnetic field of strength, $h_a$, that rotates in the x-y plane and which therefore has a component in the y-direction that is equal to ($h_a \cos \omega_a t$).

The detection light 48 interacts with the rubidium atoms 52, which are under the influence of the steady magnetic field 50, a superimposed AC carrier magnetic field 58, and the y-component of the nuclear precession field $h_a$. This interaction causes the intensity of the x-component of the transmitted light 60 to be modulated at the carrier frequency $\omega_c$ with a modulation envelope 62 at the nuclear precession frequency $\omega_a$. These light modulations are then converted into electrical signals by the silcon photodetector 38.

Referring now to FIG. 3, an NMR cell 28 was heated to a predetermined set of temperatures (°C.) within the oven 30 and retained there over a period of time for each temperature of sufficient length to measure the NMR gyro bias. The gyro bias represents the apparent change of the gyro's angular positions in degrees per a period of time even though the gyro is locked to a fixed platform. The measured values of gyro bias are shown within the squares with the vertical bars representing the computed experimental error. The sign of the bias refers to the direction of apparent rotation and here is arbitrarily chosen to be negative. Even taking into account the experimental error, it is apparent that the maximum magnitude of the bias for the particular NMR cell tested occurs at 79° C., keeping in mind that the NMR gyro bias is shown as a negative scale in FIG. 3.

The experimenter and inventor of the present invention had expected to obtain a line with no maximum or minimum. This unexpected result reflected by the rising and then falling curve of FIG. 3 indicates a point at which the gyro bias undergoes a change of direction at a particular temperature referred to herein as the "temperature turning point". By differentiating the values of this curve, it will be seen that there is one temperature at which the gyro bias is substantially zero. The differentiation of the curves is discussed in greater detail with regard to FIG. 6 below.

After the discovery of the unexpected temperature turning point which, in FIG. 3, is at 79° C., for the particular cell tested, it was determined that the oven 30 could be used to eliminate or substantially reduce the gyro bias. The oven had been previously used to maintain the NMR cell at a fixed temperature (65° C. as taught by the 4,157,495 patent at column 9, line 48), but this temperature had no relationship to gyro bias.

After the discovery of this unexpected result, a set of calculations was developed which confirmed that a plot of gyro bias versus temperature passes through a maximum, i.e. exhibits a temperature turning point. Further, it was discovered that the curves which illustrate this effect become flatter for a particular cell with a low adsorption energy value. The adsorption energy is the strength of the interaction of the gas contained in the cell with the cell wall. As shown in FIG. 4, the calculated results of six different cells having adsorption energy values between 0.15 eV and 0.20 eV was plotted for gyro bias versus cell temperature. From a review of FIG. 4, one can see that it is important to reduce the adsorption energy of a cell to as low a value as possible.

This reduction of adsorption energy may be accomplished by coating the inner surface of the cell 28 with an alkali metal hydride which may be selected from a group consisting of cesium, lithium, potassium, sodium, and rubidium. These alkali metal hydrides are deposited in accordance with the methods taught by the aforementioned co-pending patent application Ser. No. 307,995 filed, Oct. 2, 1981, by T. M. Kwon and W. P. Debley, which is assigned to the same assignee as the present invention.

In one method of producing the layer of rubidium hydride on the inner surface of container 28, the glass container is first connected to a vacuum gas filling system. After evacuation, the cell 28 is filled with the gases in the amounts previously described with the addition of approximately 10 Torr of hydrogen gas. The rubidium is added in an amount in excess of a stoichiometric mixture with respect to the hyrldrogen. The substances can be added in any convenient order. The cell 28 is then sealed, removed from the vacuum gas filling system and maintained at an elevated temperature for a time period sufficient for the hydrogen and rubidium to react to produce a rubidium hydride coating on the inner surface of the contained 28. The presence of the coating manifests itself by a clearly visible milky color on the container walls. In the embodiment of the method described, the temperature was maintained at approximately 85° C. for approximately 7 days. In other embodiments the temperature can be maintained in the range from 70° C. to 90° C. from between 4 to 14 days.

Practical temperatures can range from about 70° C. to about 250° C. At much below the lower temperature, the reaction takes too long to be practical. Much above the higher temperature, it has been determined that unreacted rubidium metal disappears, probably because of diffusion into or through the cell walls or because of a reaction with the cell walls. An additional short-coming of such a higher temperature is that impurities are driven off the cell walls, resulting in contamination of the gas mixture.

The cell is filled with various gases including rubidium and two isotopes from at least one noble gas. Also placed within the cell are buffer gases of helium and nitrogen. The noble gases include at least one of the following gases: krypton-83, krypton-85, xenon-131, and neon-21. These magnetic moment gases have a quadrupole moment. The preferred embodiment of this combination includes two odd numbered isotopes from the same noble gas, such as, xenon-129 and xenon-131, in which the ratio of xenon-129 to xenon-131 is 1 to 4. The reason for this ratio is that it takes more collisions of the rubidium with the xenon-131 to produce the same amplitude of macroscopic nuclear magnetic moment as that produced by collisions between rubidium and xenon-129. A problem with using xenon-131 is caused by the quadrupole interaction of the xenon-131 with the wall surface of the cell 28. The quadrupole interaction creates a tendency for the xenon-131 to stick or linger at the wall surface. This problem is solved by producing a cell 28 with a low adsorption energy level. An additional advantage for the use of a cell with a low adsorption energy value was unexpectedly found to be improved temperature stability of such a cell as shown by the flat curve of NMR gyro bias versus temperature generated by a cell with a low adsorption energy level in FIG. 4. The preferred embodiment has a coating of rubidium hydride on the cell wall.

Figure 5:
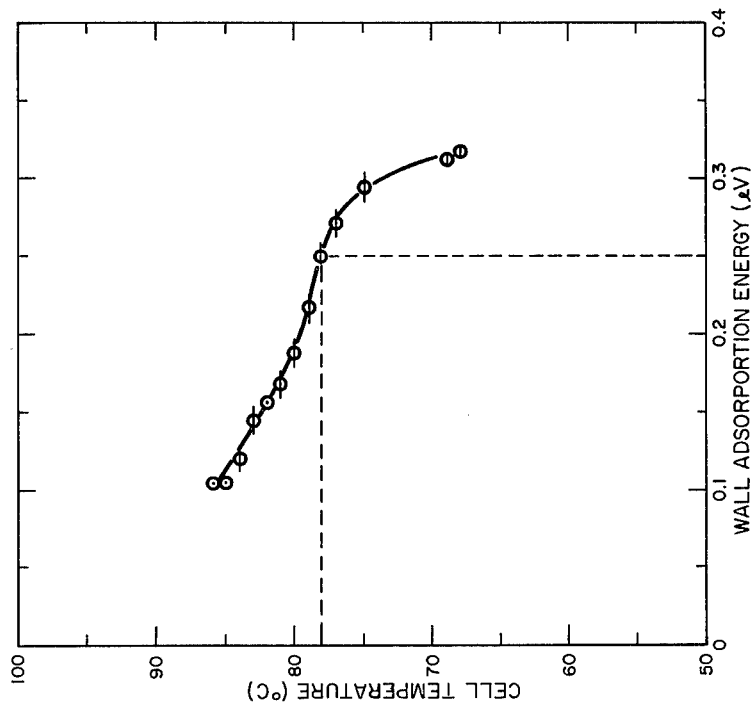
FIG. 5 shows the typical curve of cell temperature (°C.) versus wall adsorption energy (eV) for a particular NMR cell.

FIG. 5 shows a plot of the cell temperature turning point (°C.) versus wall adsorption energy (eV). This plot is a calculated value for one particular cell. It should be noted that the curve is flattest at a wall adsorption energy value of 0.25 electron volts with a corresponding temperature of 79° C.

Figure 6:
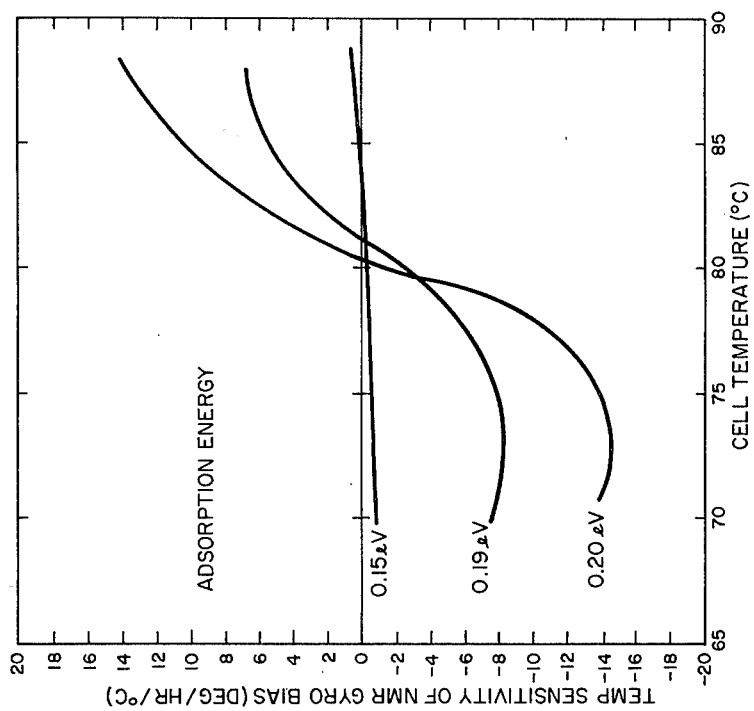
FIG. 6 shows a family of curves which represent the derivative of the curves shown in FIG. 4 plotting temperature sensitivity of an NMR gyro bias (deg/hr/°C.) versus cell temperature (°C.).

Referring now to FIG. 6, the curves shown in FIG. 4 have been differentiated and plotted for cells having an adsorption energy of 0.15, 0.19, and 0.20 electron volts (eV). Note, that the curves cross the zero line at a temperature other than 79°. For example, the curve for a cell with an adsorption energy of 0.15 electron volt appears to cross the zero temperature sensitivity line at approximately 83° C. The same curve for a cell with a 0.20 electron volt adsorption energy value crosses the zero line at approximately 81° C. The difference between the temperature here and the temperature in FIG. 3 may be explained by remembering that it is readily possible to directly measure the polarization of the rubidium which eventually translates into the measurement taken in FIG. 3. However, it is not possible to measure the adsorption energy. Adsorption or wall energy is an assumed value in the curves of FIGS. 4–6. The curves of FIG. 6, for example, represent the values obtained when one empirically establishes a value for wall energy for a particular cell. The correlation between the calculated values of FIGS. 4–6 and the measured value of FIG. 3 is sufficiently close to support the conclusion that a temperature exists for a particular cell which will produce a gyro bias versus temperature curve having a zero slope at a particular temperature. This so-called temperature turning point may be easily determined for each cell. Once determined, it is then possible to retain that cell at that temperature. Experimentation has shown that the temperature should be maintained within a range of ±0.1° C. By contrast, prior art NMR gyros require that temperature be maintained within a range of a few millidegrees Centigrade.

By observing FIG. 6, it will be noted that it is also possible to provide a servo feedback circuit which relies upon the predetermined drift of the NMR gyro bias with temperature. Such a circuit will sense the cell temperature and introduce a correction factor into the system which cancels the gyro bias drift caused by temperature change. For example, if the cell shown in the curves of FIG. 6 had an adsorption energy value of 0.20 electron volts, and was operated at a temperature turning point of 80.5° C., the temperature sensitivity of the gyro bias would be zero at the temperature turning point and near zero over a range of temperature about the temperature turning point.

Referring to FIG. 6, the change in gyro bias over a given temperature range is given by the area under the curve between the temperature points selected. An inspection of FIG. 6 shows that for the relatively large increase of temperature of 1° C. from the temperature turning point the gyro bias increases by approximately 2 angular degrees per hour. The feedback circuit, after sening the 1° C. temperature change would introduce an offsetting value of −2 angular degrees per hour into the gyro system. The importance of using the feedback circuit in this manner is that once the bias versus temperature curve is experimentally determined for a cell 28, the temperature of the cell need not be maintained at the narrow range described above. Thus, it will be appreciated that in some applications a wider temperature tolerance for the oven 30 may be obtained by utilizing a feedback circuit to introduce a predetermined corrective factor for a particular cell 28.

While the present invention has been described utilizing an NMR cell into which is introduced krypton, xenon and neon noble gases and a cell coated with cesium, lithium, potassium, sodium or rubidium, it will be understood that other noble gases and alkali metals may also be utilized.

I claim:

1. A method for reducing the temperature sensitivity of a cell used within an NMR magnetic alignment device, comprising the steps of:
    introducing into said cell a mixture of gases including at least two isotopes of at least one magnetic moment gas wherein at least one isotope has a nuclear quadrupole moment;
    varying the temperature of said cell to a predetermined series of temperature values;
    measuring the change of the bias of said cell with temperature at each of said series of predetermined temperature values to determine the established temperature at which said change of said bias with temperature of said cell reaches its minimum rate of change; and
    maintaining said cell at nearly said established temperature of minimum rate of change during operation of said magnetic alignment device.

2. A method, as claimed in claim 1, wherein said cell is a nuclear magnetic resonance cell.

3. A method, as claimed in claim 1, wherein at least one isotope of said at least one magnetic moment gas having a nuclear quadrupole moment is selected from the group consisting of krypton-83, krypton-85, xenon-131, and neon-21.

4. A method, as claimed in claim 1, wherein said at least one isotope of said at least one magnetic moment gas is xenon-129 and xenon-131.

5. A method, as claimed in claim 4, wherein said isotopes of xenon-129 and xenon-313 are present in a 1 to 4 ratio.

6. A method, as claimed in claim 5, wherein said cell is maintained at said established temperature within a range of ±0.1° C.

7. A method, as claimed in claim 1, additionally comprising the steps of:
    coating the inner walls of said cell with an alkali metal hydride to reduce the adsorption energy of said cell;
    measuring said adsorption energy of said cell; and
    selecting those cells with a low adsorption energy of between 0.1 eV to 0.25 eV.

8. A method, as claimed in claim 1, additionally comprising the steps of:
    measuring the temperature of said cell;

maintaining said cell at said established temperature to within a determined temperature range; and introducing a corrective factor to said alignment device to correct said change of said bias with change in temperature of said cell.

9. A cell for use in a magnetic alignment device, comprising:
   a container for gas;
   a magnetic moment gas retained within said container having a mixture of gases including at least two isotopes of at least one noble gas;
   an oven for heating said container; and
   means for retaining said oven at an established temperature at which the change of bias with temperature of said cell is maintained at its minimum value.

10. A cell, as claimed in claim 9, wherein said at least one isotope of said noble gas is selected from the group consisting of krypton-83, krypton-85, xenon-131, and neon-21.

11. A cell, as claimed in claim 9, wherein said at least one isotope of said noble gas consists of xenon-129 and xenon-131.

12. A cell, as claimed in claim 11, wherein said xenon-129 and xenon-131 is present in a ratio of 1 to 4.

13. A cell, as claimed in claim 9, additionally comprising:
   said container having an inner surface;
   a coating of alkali metal hydride upon said inner surface of said container;
   said alkali metal hydride selected from a group consisting of cesium, lithium, potassium, sodium and rubidium to reduce the wall energy of said cell.

14. A cell, as claimed in claim 9, additionally comprising:
   said contained having an inner surface; and
   a coating of rubidium hydride upon the inner surface of said container.

15. A cell, as claimed in claims 13 or 14, wherein said coating reduces the adsorption energy of said cell to between 0.1 and 0.25 eV; and said established temperature is between 75° C. and 85° C.

16. A cell, as claimed in claims 9 or 15, wherein said means for retaining said oven at a said established temperature maintains said temperature to within a determined temperature range of approximately ±0.1° C.

17. A cell, as claimed in claim 9, additionally comprising:
   means for measuring the temperature of said cell;
   means for maintaining said cell at said established temperature to within a determined temperature range; and
   means for introducing a corrective factor to said alignment device to correct said change of said bias with change in temperature of said cell.

* * * * *